United States Patent [19]
Zocchi et al.

[11] Patent Number: 5,942,482
[45] Date of Patent: *Aug. 24, 1999

[54] ACARICIDAL CARPET CLEANING COMPOSITION COMPRISING ESTERIFIED AND NON-ESTERIFIED ETHOXYLATED GLYCEROL MIXTURE

[75] Inventors: Germaine Zocchi, Villers-Aux-Tours, Belgium; Betty Kong, Westfield, N.J.; Myriam Mondin, Seraing; Marianne Mahieu, Ferrieres, both of Belgium

[73] Assignee: Colgate Palmolive Company, NY, N.Y.

[*] Notice: This patent is subject to a terminal disclaimer.

[21] Appl. No.: 08/938,685

[22] Filed: Sep. 26, 1997

Related U.S. Application Data

[63] Continuation-in-part of application No. 08/671,471, Jun. 28, 1996, abandoned, which is a continuation-in-part of application No. 08/553,183, Feb. 12, 1996, abandoned, which is a continuation-in-part of application No. 08/523,562, Sep. 5, 1995, which is a continuation-in-part of application No. 08/192,118, Feb. 3, 1994, abandoned, which is a continuation-in-part of application No. 08/155,317, Nov. 22, 1993, abandoned, which is a continuation-in-part of application No. 08/102,314, Aug. 4, 1993, abandoned.

[51] Int. Cl.[6] ............................... C11D 3/48; C11D 3/50; C11D 3/60

[52] U.S. Cl. ............................. 510/280; 510/101; 510/279; 510/319; 510/340; 510/342; 510/343; 510/351; 510/356; 510/360; 510/508

[58] Field of Search ................................ 510/278–80, 319, 510/342, 351, 356, 360, 361, 383, 406, 421, 424, 427, 432, 434, 102, 104, 106, 506, 101, 437, 343, 340, 508

[56] References Cited

U.S. PATENT DOCUMENTS

| | | | |
|---|---|---|---|
| 4,313,847 | 2/1982 | Chasin et al. | 252/356 |
| 4,564,632 | 1/1986 | Nonn et al. | 514/522 |
| 4,666,940 | 5/1987 | Bischoff et al. | 510/278 |
| 4,737,520 | 4/1988 | Naik et al. | 514/520 |
| 4,804,683 | 2/1989 | Steltenkamp | 514/629 |
| 4,954,338 | 9/1990 | Mattox | 514/372 |
| 5,258,408 | 11/1993 | Steltenkamp | 514/625 |
| 5,403,509 | 4/1995 | Pujol et al. | 510/535 |
| 5,529,713 | 6/1996 | Gauthier-Fournier | 510/384 |
| 5,610,130 | 3/1997 | Thomas et al. | 510/383 |
| 5,719,114 | 2/1998 | Zocchi et al. | 510/383 |

FOREIGN PATENT DOCUMENTS

89/12673  12/1989  WIPO.

*Primary Examiner*—Ardith Hertzog
*Attorney, Agent, or Firm*—Richard Nanfeldt

[57] ABSTRACT

An improvement is described in the carpet compositions which is especially effective in killing dust mites, contains an anionic detergent, an ethoxylated glycerol type compound, a hydrocarbon ingredient, at least one cosurfactant, an acaricidal agent, and water.

11 Claims, No Drawings

5,942,482

ACARICIDAL CARPET CLEANING COMPOSITION COMPRISING ESTERIFIED AND NON-ESTERIFIED ETHOXYLATED GLYCEROL MIXTURE

RELATED APPLICATION

This application is a continuation in part application of U.S. Ser. No. 8/671,471 filed Jun. 28, 1996, abandoned, which in turn is a continuation in part of U.S. Ser. No. 8/553,183 filed Feb. 12, 1996, abandoned which in turn is a continuation in part application of U.S. Ser. No. 8/523,562 filed Sep. 5, 1995, pending which in turn is a continuation in part application of U.S. Ser. No. 8/192,118 filed Feb. 3, 1994, abandoned which in turn is a continuation in part application of U.S. Ser. No. 8/155,317 filed Nov. 22, 1993, abandoned which in turn is a continuation in part application of U.S. Ser. No. 8/102,314 filed Aug. 4, 1993 abandoned.

FIELD OF THE INVENTION

This invention relates to an improved carpet liquid cleaner can be in the form of a liquid crystal or a microemulsion designed in particular for cleaning carpets and which is effective in killing dust mites.

BACKGROUND OF THE INVENTION

In recent years all-purpose liquid detergents have become widely accepted for cleaning hard surfaces, e.g., painted woodwork and panels, tiled walls, wash bowls, bathtubs, linoleum or tile floors, washable wall paper, etc.. Such all-purpose liquids comprise clear and opaque aqueous mixtures of water-soluble synthetic organic detergents and water-soluble detergent builder salts. In order to achieve comparable cleaning efficiency with granular or powdered all-purpose cleaning compositions, use of water-soluble inorganic phosphate builder salts was favored in the prior art all-purpose liquids. For example, such early phosphate-containing compositions are described in U.S. Pat. Nos. 2,560,839; 3,234,138; 3,350,319; and British Patent No. 1,223,739.

In view of the environmentalist's efforts to reduce phosphate levels in ground water, improved all-purpose liquids containing reduced concentrations of inorganic phosphate builder salts or non-phosphate builder salts have appeared. A particularly useful self-opacified liquid of the latter type is described in U.S. Pat. No. 4,244,840.

However, these prior art all-purpose liquid detergents containing detergent builder salts or other equivalent tend to leave films, spots or streaks on cleaned unrinsed surfaces, particularly shiny surfaces. Thus, such liquids require thorough rinsing of the cleaned surfaces which is a time-consuming chore for the user.

In order to overcome the foregoing disadvantage of the prior art all-purpose liquid, U.S. Pat. No. 4,017,409 teaches that a mixture of paraffin sulfonate and a reduced concentration of inorganic phosphate builder salt should be employed. However, such compositions are not completely acceptable from an environmental point of view based upon the phosphate content. On the other hand, another alternative to achieving phosphate-free all-purpose liquids has been to use a major proportion of a mixture of anionic and nonionic detergents with minor amounts of glycol ether solvent and organic amine as shown in U.S. Pat. No. 3,935,130. Again, this approach has not been completely satisfactory and the high levels of organic detergents necessary to achieve cleaning cause foaming which, in turn, leads to the need for thorough rinsing which has been found to be undesirable to today's consumers.

Another approach to formulating hard surfaced or all-purpose liquid detergent composition where product homogeneity and clarity are important considerations involves the formation of oil-in-water (o/w) microemulsions which contain one or more surface-active detergent compounds, a water-immiscible solvent (typically a hydrocarbon solvent), water and a "cosurfactant" compound which provides product stability. By definition, an o/w microemulsion is a spontaneously forming colloidal dispersion of "oil" phase particles having a particle size in the range of 25 Å to 800 Å in a continuous aqueous phase.

In view of the extremely fine particle size of the dispersed oil phase particles, microemulsions are transparent to light and are clear and usually highly stable against phase separation.

Patent disclosures relating to use of grease-removal solvents in o/w microemulsions include, for example, European Patent Applications EP 0137615 and EP 0137616—Herbots et al; European Patent Application EP 0160762—Johnston et al; and U.S. Pat. No. 4,561,991—Herbots et al. Each of these patent disclosures also teaches using at least 5% by weight of grease-removal solvent.

It also is known from British Patent Application GB 2144763A to Herbots et al, published Mar. 13, 1985, that magnesium salts enhance grease-removal performance of organic grease-removal solvents, such as the terpenes, in o/w microemulsion liquid detergent compositions. The compositions of this invention described by Herbots et al. require at least 5% of the mixture of grease-removal solvent and magnesium salt and preferably at least 5% of solvent (which may be a mixture of water-immiscible non-polar solvent with a sparingly soluble slightly polar solvent) and at least 0.1% magnesium salt.

However, since the amount of water immiscible and sparingly soluble components which can be present in an o/w microemulsion, with low total active ingredients without impairing the stability of the microemulsion is rather limited (for example, up to 18% by weight of the aqueous phase), the presence of such high quantities of grease-removal solvent tend to reduce the total amount of greasy or oily soils which can be taken up by and into the microemulsion without causing phase separation.

The following representative prior art patents also relate to liquid detergent cleaning compositions in the form of o/w microemulsions: U.S. Pat. Nos. 4,472,291—Rosario; 4,540,448—Gauteer et al; 3,723,330—Sheflin; etc.

Liquid detergent compositions which include terpenes, such as d-limonene, or other grease-removal solvent, although not disclosed to be in the form of o/w microemulsions, are the subject matter of the following representative patent documents: European Patent Application 0080749; British Patent Specification 1,603,047; and U.S. Pat. Nos. 4,414,128; and 4,540,505. For example, U.S. Pat. No. 4,414,128 broadly discloses an aqueous liquid detergent composition characterized by, by weight:

(a) from 1% to 20% of a synthetic anionic, nonionic, amphoteric or zwitterionic surfactant or mixture thereof;

(b) from 0.5% to 10% of a mono- or sesquiterpene or mixture thereof, at a weight ratio of (a):(b) lying in the range of 5:1 to 1:3; and (c) from 0.5% 10% of a polar solvent having a solubility in water at 15° C. in the range of from 0.2% to 10%. Other ingredients present in the formulations disclosed in this patent include from 0.05% to 2% by weight of an alkali metal, ammonium or alkanolammonium soap of a $C_{13}$–$C_{24}$ fatty acid; a calcium sequestrant from 0.5% to 13% by weight; non-aqueous solvent, e.g., alcohols and glycol ethers, up to 10% by weight; and hydrotropes, e.g., urea, ethanolamines, salts of lower alkylaryl sulfonates, up to 10% by weight. All of the formulations shown in the Examples of this patent include relatively large amounts of detergent builder salts which are detrimental to surface shine.

Furthermore, the present inventors have observed that in formulations containing grease-removal assisting magnesium compounds, the addition of minor amounts of builder salts, such as alkali metal polyphosphates, alkali metal carbonates, nitrilotriacetic acid salts, and so on, tends to make it more difficult to form stable microemulsion systems.

U.S. Pat. No. 5,082,584 discloses a microemulsion composition having an anionic surfactant, a cosurfactant, nonionic surfactant, perfume and water; however, these compositions do not possess the low ecotoxicity profile and the improved interfacial tension properties as exhibited by the compositions of the instant invention.

British Patent No 1,453,385 discloses polyesterified nonionic surfactants similar to the polyesterified nonionic surfactants of the instant invention. However, these nonionic surfactants of British Patent 1,453,385 do not disclose the formula (II) portion of the instant composition. Additionally, the formulated compositions of British Patent 1,453,385 fail to disclose the critical limitations of the instant invention.

A number of patents teach esterified ethoxylated glycerol compounds for various applications. These patents are Great Britain 1,453,385; Japan 59-1600 and Japan 58-206693 and European Patent Application 0586,323A1. These publications fail to appreciate that a mixture of esterified ethoxylated glycerol and nonesterified ethoxylated glycerol, when used in a hard surface cleaning composition, functions as a grease release agent.

U.S. Pat. No. 4,666,940 discloses acaricidal agents in combination with solid components that leave a residue on the surface being treated.

SUMMARY OF THE INVENTION

The present invention provides an improved, liquid carpet cleaning composition having improved interfacial tension which can be in the form of a liquid crystal or a microemulsion and is suitable for cleaning carpets, hard surfaces such as plastic, vitreous and metal surfaces having a shiny finish. More particularly, the improved cleaning compositions are useful in killing dust mites.

The instant compositions are more friendly for the environment due to the low ecotoxicity of the ethoxylated glycerol type compounds (as defined below) used in the instant compositions.

The compositions of the instant invention have an ecotoxocity value as measured by the LC 50 test as deferred by The Organization for Economic Cooperation and Development (OECD)(of which the United States is a member) in OECD Test No. 202 of at least 0.18 ml/L measured on Daphniae microorganisms.

In one aspect, the invention generally provides a stable, carpet cleaning composition which can be in the form of a microemulsion having an aqueous phase and an oil phase. The microemulsion includes, on a weight basis:

from 0.05% to 5% of an acaricidal agent;
from 0.1% to 20% of an anionic surfactant;
from 0.1% to 50% of at least one water-mixable cosurfactant having either limited ability or substantially no ability to dissolve oily or greasy soil;

0.1% to 20% of a compound which is a mixture of a partially esterified ethoxylated polyhydric alcohol, a fully esterified ethoxylated polyhydric alcohol and a nonesterified ethoxylated polyhydric alcohol, said mixture being (herein after referred to as an ethoxylated glycerol type compound);

0 to 4% of magnesium sulfate heptahydrate;
0.1 to 10.0% of a perfume, essential oil or water insoluble hydrocarbon;
0 to 3 wt. % of an alkali metal silicate;
0 to 20 wt. % of a hydrocarbon propellant; and balance being water, said proportions being based upon the total weight of the composition, wherein the composition does not contain any zwitterionic surfactants which would destroy the microemulsion or condensate products of a primary alkanol and ethylene oxide and wherein the composition does not contain a solid component having a mean particle size of 2 to 100 microns which would leave a pulverulent residue on the surface being treated or quartz, sand, siliceous earth, metal carbonate, $SiO_2$, amorphous silica, silicates, polyacrylates, xanthan gum. Explicitly excluded from the instant compositions are aliphatic alcohols, alkyl aryl alcohols such as benzyl alcohol and phenylethyl alcohol, alkanol amines, amines, polyhexamethylene biquamide hydrochloride, didecyl dimethyl ammonium chloride, benzyalkonium chloride, isopropyl alcohol and N-lower alkyl neoalkanolamides such as methyl neodecamide and N, N-diethyl-meta-toluamide.

The dispersed oil phase of the microemulsion is composed essentially of the water-immiscible or hardly water-soluble perfume.

Quite surprisingly although the perfume is not, per se, a solvent for greasy or oily soil,—even though some perfumes may, in fact, contain as much as 80% of terpenes which are known as good grease solvents—the inventive compositions in dilute form have the capacity to solubilize up to 10 times or more of the weight of the perfume of oily and greasy soil, which is removed or loosened from the hard surface by virtue of the action of the anionic and nonionic surfactants, said soil being taken up into the oil phase of the o/w microemulsion.

In second aspect, the invention generally provides highly concentration carpet microemulsion compositions in the form of either an oil-in-water (o/w) microemulsion or a water-in-oil (w/o) microemulsion which when diluted with additional water before use can form dilute o/w microemulsion compositions. Broadly, the concentrated carpet cleaning microemulsion compositions contain, by weight, 0.1% to 20% of an anionic surfactant, 0.5% to 5% of an acaricidal agent; 0.1% to 20% of an ethoxylated glycerol type compound, 0% to 2.5% of a fatty acid, 0.1% to 10% of perfume or water insoluble hydrocarbon having 6 to 18 carbon atoms, 0.1% to 50% of a cosurfactant, 0 to 20% of a hydrocarbon propellant, and 20% to 97% of water.

In a third aspect of the invention, liquid crystal carpet cleaning compositions are provided which comprise by weight 0 to 20% of an anionic surfactant, 0.1% to 20% of an ethoxylated glycerol type compound, 0.05% to 5% of an acaricidal agent, 0 to 2.5% of a fatty acid, 0.5% to 10% of a perfume, 0 to 20% of a hydrocarbon propellant, 1% to 50% of at least one cosurfactant and the balance being water.

DETAILED DESCRIPTION OF THE INVENTION

The present invention relates to a carpet cleaning composition approximately by weight: 0.1% to 20% of an anionic surfactant, 0.05% to 5% of an acaricidal agent, 0.1% to 50% of at least one cosurfactant, 0.1% to 20% of an ethoxylated glycerol type compound, 0 to 3% of an alkali metal silicate, 0.1% to 10% of a water insoluble hydrocarbon, essential oil or a perfume and the balance being water.

According to the present invention, the role of the hydrocarbon is provided by a non-water-soluble perfume. Typically, in aqueous based compositions the presence of a solubilizers, such as alkali metal lower alkyl aryl sulfonate hydrotrope, triethanolamine, urea, etc., is required for perfume dissolution, especially at perfume levels of 1% and higher, since perfumes are generally a mixture of fragrant essential oils and aromatic compounds which are generally not water-soluble. Therefore, by incorporating the perfume into the aqueous cleaning composition as the oil (hydrocarbon) phase of the ultimate o/w microemulsion composition, several different important advantages are achieved.

First, the cosmetic properties of the ultimate cleaning composition are improved: the compositions are both clear (as a consequence of the formation of a microemulsion) and highly fragranced (as a consequence of the perfume level).

Second, the need for use of solubilizers, which do not contribute to cleaning performance, is eliminated.

As used herein and in the appended claims the term "perfume" is used in its ordinary sense to refer to and include any non-water soluble fragrant substance or mixture of substances including natural (i.e., obtained by extraction of flower, herb, blossom or plant), artificial (i.e., mixture of natural oils or oil constituents) and synthetically produced substance) odoriferous substances. Typically, perfumes are complex mixtures of blends of various organic compounds such as alcohols, aldehydes, ethers, aromatic compounds and varying amounts of essential oils (e.g., terpenes) such as from 0% to 80%, usually from 10% to 70% by weight, the essential oils themselves being volatile odoriferous compounds and also serving to dissolve the other components of the perfume.

In the present invention the precise composition of the perfume is of no particular consequence to cleaning performance so long as it meets the criteria of water immiscibility and having a pleasing odor. Naturally, of course, especially for cleaning compositions intended for use in the home, the perfume, as well as all other ingredients, should be cosmetically acceptable, i.e., non-toxic, hypoallergenic, etc.. The instant compositions show a marked improvement in ecotoxocity as compared to existing commercial products.

The hydrocarbon such as a perfume is present in the dilute o/w microemulsion in an amount of from 0.1% to 10% by weight, preferably from 0.4% to 6.0% by weight, especially preferably from 0.5% to 3.0% by weight. In the case of the liquid crystal one need at least 0.5 weight % of perfume, more preferably 1 weight %. If the hydrocarbon (perfume) is added in amounts more than 10% by weight, the cost is increased without any additional cleaning benefit and, in fact, with some diminishing of cleaning performance insofar as the total amount of greasy or oily soil which can be taken up in the oil phase of the microemulsion will decrease proportionately.

Furthermore, although superior grease removal performance will be achieved for perfume compositions not containing any terpene solvents, it is apparently difficult for perfumers to formulate sufficiently inexpensive perfume compositions for products of this type (i.e., very cost sensitive consumer-type products) which includes less than 20%, usually less than 30%, of such terpene solvents.

Thus, merely as a practical matter, based on economic consideration, the dilute o/w microemulsion detergent cleaning compositions of the present invention may often include as much as 0.2% to 7% by weight, based on the total composition, of terpene solvents introduced thereunto via the perfume component. However, even when the amount of terpene solvent in the cleaning formulation is less than 1.5% by weight, such as up to 0.6% by weight or 0.4% by weight or less, satisfactory grease removal and oil removal capacity is provided by the inventive diluted o/w microemulsions.

Thus, for a typical formulation of a diluted o/w microemulsion according to this invention a 20 milliliter sample of o/w microemulsion containing 1% by weight of perfume will be able to solubilize, for example, up to 2 to 3 ml of greasy and/or oily soil, while retaining its form as a microemulsion, regardless of whether the perfume contains 0%, 0.1%, 0.2%, 0.3%, 0.4%, 0.5%, 0.6%, 0.7% or 0.8% by weight of terpene solvent. In other words, it is an essential feature of the compositions of this invention that grease removal is a function of the result of the microemulsion, per se, and not of the presence or absence in the microemulsion of a "greasy soil removal" type of solvent.

In place of the perfume one can employ a water insoluble suitable essential oils which are selected from the group consisting of: Anethole 20/21 natural, Aniseed oil china star, Aniseed oil globe brand, Balsam (Peru), Basil oil (India), Black pepper oil, Black pepper oleoresin 40/20, Bois de Rose (Brazil) FOB, Borneol Flakes (China), Camphor oil, White, Camphor powder synthetic technical, Cananga oil (Java), Cardamom oil, Cassia oil (China), Cedarwood oil (China) BP, Cinnamon bark oil, Cinnamon leaf oil, Citronella oil, Clove bud oil, Clove leaf, Coriander (Russia), Coumarin 69° C. (China), Cyclamen Aldehyde, Diphenyl oxide, Ethyl vanilin, Eucalyptol, Eucalyptus oil, Eucalyptus citriodora, Fennel oil, Geranium oil, Ginger oil, Ginger oleoresin (India), White grapefruit oil, Guaiacwood oil, Gurjun balsam, Heliotropin, Isobornyl acetate, Isolongifolene, Juniper berry oil, L-methyl acetate, Lavender oil, Lemon oil, Lemongrass oil, Lime oil distilled, Litsea Cubeba oil, Longifolene, Menthol crystals, Methyl cedryl ketone, Methyl chavicol, Methyl salicylate, Musk ambrette, Musk ketone, Musk xylol, Nutmeg oil, Orange oil, Patchouli oil, Peppermint oil, Phenyl ethyl alcohol, Pimento berry oil, Pimento leaf oil, Rosalin, Sandalwood oil, Sandenol, Sage oil, Clary sage, Sassafras oil, Spearmint oil, Spike lavender, Tagetes, Tea tree oil, Vanilin, Vetyver oil (Java), Wintergreen, paraffin or isoparaffin having 6 to 18 carbon at a concentration of 0.4 to 8.0 wt. percent, more preferably 0.4 to 3.0 wt. %. 50 to 70 wt. % of the perfume or essential oil may exhibit acaricidal activity.

The water-soluble organic surfactants which are used in forming the carpet cleaning compositions of this invention may be selected from the group consisting of water-soluble, non-soap, anionic surfactants mixed with optionally a fatty acid and a solubilizing agent which is a partially esterified ethoxylated polyhydric alcohol such as a partially esterified ethoxylated glycerol.

Although conventional nonionic surfactants can be used in the instant compositions, the employment of such conventional nonionic in the instant composition will decrease the environmental profile of the composition as well as having an adverse effect on the grease release and grease+ particulate soil removal properties of the composition.

Regarding the anionic surfactant present in the microemulsions any of the conventionally used water-soluble anionic surfactants or mixtures of said anionic detergents and anionic detergents can be used in this invention. As used herein the term "anionic surfactant" is intended to refer to the class of anionic and mixed anionic-nonionic surfactants providing detersive action.

Suitable water-soluble non-soap, anionic surfactants include those surface-active or detergent compounds which contain an organic hydrophobic group containing generally 8 to 26 carbon atoms and preferably 10 to 18 carbon atoms in their molecular structure and at least one water-solubilizing group selected from the group of sulfonate, sulfate and carboxylate so as to form a water-soluble surfactant. Usually, the hydrophobic group will include or comprise a $C_8$–$C_{22}$ alkyl, alkyl or acyl group. Such surfactants are employed in the form of water-soluble salts and the salt-forming cation usually is selected from the group consisting of sodium, potassium, ammonium, magnesium and mono-, di- or tri-$C_2$–$C_3$ alkanolammonium, with the sodium, magnesium and ammonium cations again being preferred.

Examples of suitable sulfonated anionic surfactants are the well known higher alkyl mononuclear aromatic sulfonates such as the higher alkyl benzene sulfonates containing from 10 to 16 carbon atoms in the higher alkyl group in a straight or branched chain, $C_8$–$C_{15}$ alkyl toluene sulfonates and $C_8$–$C_{15}$ alkyl phenol sulfonates.

A preferred sulfonate is linear alkyl benzene sulfonate having a high content of 3- (or higher) phenyl isomers and a correspondingly low content (well below 50%) of 2- (or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position is correspondingly low. Particularly preferred materials are set forth in U.S. Pat. No. 3,320,174.

Other suitable anionic surfactants are the olefin sulfonates, including long-chain alkene sulfonates, long-chain hydroxyalkane sulfonates or mixtures of alkene sulfonates and hydroxyalkane sulfonates. These olefin sulfonate surfactants may be prepared in a known manner by the reaction of sulfur trioxide ($SO_3$) with long-chain olefins containing 8 to 25, preferably 12 to 21 carbon atoms and having the formula $RCH=CHR_1$ where R is a higher alkyl group of 6 to 23 carbons and $R_1$ is an alkyl group of 1 to 17 carbons or hydrogen to form a mixture of sultones and alkene sulfonic acids which is then treated to convert the sultones to sulfonates. Preferred olefin sulfonates contain from 14 to 16 carbon atoms in the R alkyl group and are obtained by sulfonating an alpha-olefin.

Other examples of suitable anionic sulfonate surfactants are the paraffin sulfonates containing 10 to 20, preferably 13 to 17, carbon atoms. Primary paraffin sulfonates are made by reacting long-chain alpha olefins and bisulfites and paraffin sulfonates having the sulfonate group distributed along the paraffin chain are shown in U.S. Pat. Nos. 2,503,280; 2,507,088; 3,260,744; 3,372,188; and German Patent 735, 096.

Examples of satisfactory anionic sulfate surfactants are the $C_8$–$C_{18}$ alkyl sulfate salts and the $C_8$–$C_{18}$ alkyl sulfate salts and the $C_8$–$C_{18}$ alkyl ether polyethenoxy sulfate salts having the formula $R(OC_2H_4)_n OSO_3M$ wherein n is 1 to 12, preferably 1 to 5, and M is a solubilizing cation selected from the group consisting of sodium, potassium, ammonium, magnesium and mono-, di- and triethanol ammonium ions. The alkyl sulfates may be obtained by sulfating the alcohols obtained by reducing glycerides of coconut oil or tallow or mixtures thereof and neutralizing the resultant product. On the other hand, the alkyl ether polyethenoxy sulfates are obtained by sulfating the condensation product of ethylene oxide with a $C_8$–$C_{18}$ alkanol and neutralizing the resultant product. The alkyl ether polyethenoxy sulfates differ from one another in the number of moles of ethylene oxide reacted with one mole of alkanol. Preferred alkyl sulfates and preferred alkyl ether polyethenoxy sulfates contain 10 to 16 carbon atoms in the alkyl group.

The $C_8$–$C_{12}$ alkylphenyl ether polyethenoxy sulfates containing from 2 to 6 moles of ethylene oxide in the molecule also are suitable for use in the inventive compositions. These detergents can be prepared by reacting an alkyl phenol with 2 to 6 moles of ethylene oxide and sulfating and neutralizing the resultant ethoxylated alkylphenol.

Obviously, these anionic surfactants will be present either in acid form or salt form depending upon the pH of the final composition, with salt forming cation being the same as for the other anionic detergents.

Of the foregoing non-soap anionic surfactants, the preferred surfactants are the $C_9$–$C_{15}$ linear alkylbenzene sulfonates and the $C_{13}$–$C_{17}$ paraffin or alkane sulfonates. Particularly, preferred compounds are sodium $C_{10}$–$C_{13}$ alkylbenzene sulfonate and sodium $C_{13}$–$C_{17}$ alkane sulfonate.

Generally, the proportion of the nonsoap-anionic surfactant will be in the range of 0.1% to 20.0%, preferably from 1% to 7%, by weight of the carpet cleaning composition.

The instant composition contains a composition (herein after referred to as ethoxylated glycerol type compound) which is a mixture of a fully esterified ethoxylated polyhydric alcohol, a partially esterified ethoxylated polyhydric alcohol and a nonesterified ethoxylated polyhydric alcohol, wherein the preferred polyhydric alcohol is glycerol, and the compound is Formula (I)

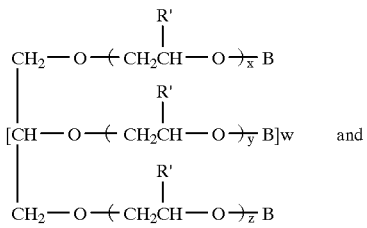

and

Formula (II)

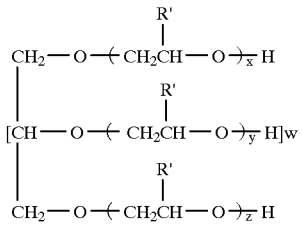

wherein w equals one to four, most preferably one, B is selected from the group consisting of hydrogen or a group represented by:

wherein R is selected from the group consisting of alkyl group having 6 to 22 carbon atoms, more preferably 11 to 15 carbon atoms and alkenyl groups having 6 to 22 carbon atoms, more preferably 11 to 15 carbon atoms, wherein a hydrogenated tallow alkyl chain or a coco alkyl chain is most preferred, wherein at least one of the B groups is represented by said

and R' is selected from the group consisting of hydrogen and methyl groups; x, y and z have a value between 0 and 60, more preferably 0 to 40, provided that (x+y+z) equals 2 to 100, preferably 4 to 24 and most preferably 4 to 19, wherein in Formula (I) the weight ratio of monoester/diester/triester is 45 to 90/5 to 40/1 to 20, more preferably 50 to 90/9 to 32/1 to 12, wherein the weight ratio of Formula (I) to Formula (II) is a value between 3 to 0.02, preferably 3 to 0.1, most preferably 1.5 to 0.2, wherein it is most preferred that there is more of Formula (II) than Formula (I) in the mixture that forms the compound.

The ethoxylated glycerol type compound used in the instant composition is manufactured by the Kao Corporation and sold under the trade name Levenol such as Levenol F-200 which has an average EO of 6 and a molar ratio of coco fatty acid to glycerol of 0.55 or Levenol V501/2 which has an average EO of 17 and a molar ratio of tallow fatty acid to glycerol of 1.0. It is preferred that the molar ratio of the fatty acid to glycerol is less than 1.7, more preferably less than 1.5 and most preferably less than 1.0. The ethoxylated glycerol type compound has a molecular weight of 400 to 1600, and a pH (50 grams/liter of water) of 5–7. The Levenol compounds are substantially non irritant to human skin and have a primary biodegradabillity higher than 90% as measured by the Wickbold method Bias-7d.

Two examples of the Levenol compounds are Levenol V-501/2 which has 17 ethoxylated groups and is derived from tallow fatty acid with a fatty acid to glycerol ratio of 1.0 and a molecular weight of 1465 and Levenol F-200 has 6 ethoxylated groups and is derived from coco fatty acid with a fatty acid to glycerol ratio of 0.55. Both Levenol F-200 and Levenol V-501/2 are composed of a mixture of Formula (I) and Formula (II). The Levenol compounds has ecoxicity values of algae growth inhibition>100 mg/liter; acute toxicity for Daphniae>100 mg/liter and acute fish toxicity>100 mg/liter. The Levenol compounds have a ready biodegradability higher than 60% which is the minimum required value according to OECD 301B measurement to be acceptably biodegradable.

Polyesterified nonionic compounds also useful in the instant compositions are Crovol PK-40 and Crovol PK-70 manufactured by Croda GMBH of the Netherlands. Crovol PK-40 is a polyoxyethylene (12) Palm Kernel Glyceride which has 12 EO groups. Crovol PK-70 which is preferred is a polyoxyethylene (45) Palm Kernel Glyceride have 45 EO groups.

In the carpet cleaning compositions the ethoxylated glycerol type compounds or the polyesterified nonionic compounds will be present in admixture with the anionic surfactant. The proportion of the ethoxylated glycerol type compound or the polyesterified nonionic solubilizing agent based upon the weight of the carpet cleaning composition will be 0.1% to 20%, more preferably 0.5% to 10%, most preferably 0.5% to 6% by weight.

Furthermore, in the more preferred compositions the weight ratio of nonsoap anionic surfactant to the ethoxylated glycerol type compound will be in the range of 3:1 to 1:3 with especially good results being obtained at a weight ratio of 2:1.

The compounds found to provide highly suitable cosurfactants for the carpet cleaning microemulsion over temperature ranges extending from 5° C. to 43° C. for instance are glycerol, ethylene glycol, water-soluble polyethylene glycols having a molecular weight of 300 to 1000, polypropylene glycol of the formula $HO(CH_3CHCH_2O)_nH$ wherein n is a number from 2 to 18, mixtures of polyethylene glycol and polypropyl glycol (Synalox) and mono $C_1$–$C_6$ alkyl ethers and esters of ethylene glycol and propylene glycol having the structural formulas $R(X)_nOH$ and $R_1(X)_nOH$ wherein R is $C_1$–$C_6$ alkyl group, $R_1$ is $C_2$–$C_4$ acyl group, X is $(OCH_2CH_2)$ or $(OCH_2(CH_3)CH)$ and n is a number from 1 to 4, diethylene glycol, triethylene glycol, an alkyl lactate, wherein the alkyl group has 1 to 6 carbon atoms, 1methoxy-2-propanol, 1methoxy-3-propanol, and 1methoxy 2-, 3- or 4-butanol.

Representative members of the polypropylene glycol include dipropylene glycol and polypropylene glycol having a molecular weight of 200 to 1000, e.g., polypropylene glycol 400. Other satisfactory glycol ethers are ethylene glycol monobutyl ether (butyl cellosolve), diethylene glycol monobutyl ether (butyl carbitol), triethylene glycol monobutyl ether, mono, di, tri propylene glycol monobutyl ether, tetraethylene glycol monobutyl ether, mono, di, tripropylene glycol monomethyl ether, propylene glycol monomethyl ether, ethylene glycol monohexyl ether, diethylene glycol monohexyl ether, propylene glycol tertiary butyl ether, ethylene glycol monoethyl ether, ethylene glycol monomethyl ether, ethylene glycol monopropyl ether, ethylene glycol monopentyl ether, diethylene glycol monomethyl ether, diethylene glycol monoethyl ether, diethylene glycol monopropyl ether, diethylene glycol monopentyl ether, triethylene glycol monomethyl ether, triethylene glycol monoethyl ether, triethylene glycol monopropyl ether, triethylene glycol monopentyl ether, triethylene glycol monohexyl ether, mono, di, tripropylene glycol monoethyl ether , mono, di tripropylene glycol monopropyl ether, mono, di, tripropylene glycol monopentyl ether, mono, di, tripropylene glycol monohexyl ether, mono, di, tributylene glycol mono methyl ether, mono, di, tributylene glycol monoethyl ether, mono, di, tributylene glycol monopropyl ether, mono, di, tributylene glycol monobutyl ether, mono, di, tributylene glycol monopentyl ether and mono, di, tributylene glycol monohexyl ether, ethylene glycol monoacetate and dipropylene glycol propionate. When these glycol type cosurfactants are at a concentration of about 1.0 to about 14 weight %, more preferably about 2.0 weight % to about 10 weight % in combination with a water insoluble hydrocarbon at a concentration of at least 0.5 weight %, more preferably 1.5 weight % one can form a microemulsion composition. When these glycol type cosurfactants are at a concentration of at least 1.0 weight %, more preferably at least 2.0 weight % in combination with a perfume at a concentration of at least 0.5 weight %, more preferably 1.5 weight % one can form a liquid crystal carpet cleaning composition.

Still other classes of cosurfactant compounds providing stable microemulsion carpet cleaning compositions at low and elevated temperatures are the mono-, di- and triethyl esters of phosphoric acid such as triethyl phosphate.

The amount of cosurfactant required to stabilize the carpet cleaning compositions will, of course, depend on such factors as the surface tension characteristics of the cosurfactant, the type and amounts of the primary surfactants and perfumes, and the type and amounts of any other additional ingredients which may be present in the composition and which have an influence on the thermodynamic factors enumerated above. Generally, amounts of cosurfactant in the range of from 0.1% to 50%, preferably from 0.5% to 15%, especially preferably from 1% to 7%, by weight provide stable carpet cleaning microemulsions for the above-described levels of primary surfactants and perfume and any other additional ingredients as described below.

The acaricidal agent is used in the carpet cleaning composition, microemulsion composition, liquid crystal composition or all purpose hard surface cleaning composition at a concentration of about 0.05 to 5.0 wt. %, more preferably 0.075 to 3 wt. %. The acaricidal agent is selected from the group consisting of

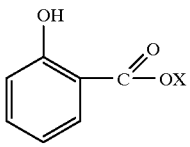

wherein x=

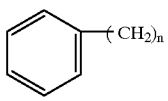

or a $C_6$–$C_{14}$ alkyl group, wherein n equals 1 to 3;

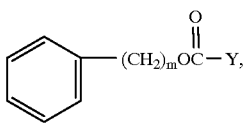

wherein m=1 to 3 and x is a $C_1$ to $C_6$ alkyl group

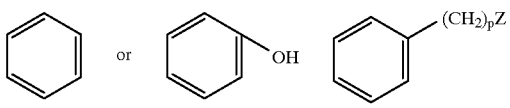

wherein p=1 to 3 and Z is a

group; carvone; citral limarome; 50 wt. thymol in benzyl benzoate; alpha pinene;citronellol dextro;hedione; linalool citronella; eucalyptus globulux; thyme white; lavandin oil grosso; a $C_6$ to $C_{14}$ aldehyde such as methyl nonyl aldehyde, hexylcinnamic aldehyde; litsea cubebaoil; 50 wt. % of camphor white in benzyl benzoate; terpenolene; rosemary oil. terpineol and verdox; 50 wt. % of menthol in benzyl benzoate. Especially preferred acaricidal agents are benzyl benzoate, benzyl alcohol, phenyl ethyl benzoate, benzaldehyde, carvone, methyl salicylate, citral lemarome, 50 wt. % of thymol in benzyl benzoate, 50 wt. % of camphor white in benzyl benzoate and 50 wt. % of menthol in benzyl benzoate.

The instant carpet cleaning can contain 0 to about 3 wt. %, more preferably about 0.1 to about 2 wt. % of an alkali metal silicate having an alkali metal oxide; $SiO_2$ ratio of at least 1:1 such as sodium silicate ($Na_2O$; $SiO_2$ of 1:3.26).

The present invention can also contain 0 to about 20 wt. %, more preferably about 1 wt. % to about 15 wt. % of a hydrocarbon propellant.

The final essential ingredient in the inventive carpet cleaning compositions having improved interfacial tension properties is water. The proportion of water in the compositions generally is in the range of 20% to 97%, preferably 70% to 97% by weight of the usual diluted o/w microemulsion composition.

In addition to the above-described essential ingredients required for the formation of the carpet cleaning composition, the compositions of this invention may often and preferably do contain one or more additional ingredients which serve to improve overall product performance.

One such ingredient is an inorganic or organic salt of oxide of a multivalent metal cation, particularly $Mg^{++}$. The metal salt or oxide provides several benefits including improved cleaning performance in dilute usage, particularly in soft water areas, and minimized amounts of perfume required to obtain the microemulsion state. Magnesium sulfate, either anhydrous or hydrated (e.g., heptahydrate), is especially preferred as the magnesium salt. Good results also have been obtained with magnesium oxide, magnesium chloride, magnesium acetate, magnesium propionate and magnesium hydroxide. These magnesium salts can be used with formulations at neutral or acidic pH since magnesium hydroxide will not precipitate at these pH levels.

Although magnesium is the preferred multivalent metal from which the salts (inclusive of the oxide and hydroxide) are formed, other polyvalent metal ions also can be used provided that their salts are nontoxic and are soluble in the aqueous phase of the system at the desired pH level. Thus, depending on such factors as the pH of the system, the nature of the primary surfactants and cosurfactant, and so on, as well as the availability and cost factors, other suitable polyvalent metal ions include aluminum, copper, nickel, iron, calcium, etc. It should be noted, for example, that with the preferred paraffin sulfonate anionic detergent calcium salts will precipitate and should not be used. It has also been found that the aluminum salts work best at pH below 5 or when a low level, for example 1 weight percent, of citric acid is added to the composition which is designed to have a neutral pH. Alternatively, the aluminum salt can be directly added as the citrate in such case. As the salt, the same general classes of anions as mentioned for the magnesium salts can be used, such as halide (e.g., bromide, chloride), sulfate, nitrate, hydroxide, oxide, acetate, propionate, etc.

Preferably, in the dilute compositions the metal compound is added to the composition in an amount sufficient to provide at least a stoichiometric equivalence between the anionic surfactant and the multivalent metal cation. For example, for each gram-ion of Mg++ there will be 2 gram moles of paraffin sulfonate, alkylbenzene sulfonate, etc., while for each gram-ion of $Al^{3+}$ there will be 3 gram moles of anionic surfactant. Thus, the proportion of the multivalent salt generally will be selected so that one equivalent of compound will neutralize from 0.1 to 1.5 equivalents, preferably 0.9 to 1.4 equivalents, of the acid form of the anionic surfactant.

At higher concentrations of anionic surfactant, the amount of multivalent salt will be in range of 0.5 to 1 equivalents per equivalent of anionic surfactant.

The carpet cleaning compositions can include from 0% to 2.5%, preferably from 0.1% to 2.0% by weight of the composition of a $C8$–$C_{22}$ fatty acid or fatty acid soap as a foam suppressant. The addition of fatty acid or fatty acid soap provides an improvement in the rinseability of the composition whether applied in neat or diluted form. Generally, however, it is necessary to increase the level of cosurfactant to maintain product stability when the fatty acid or soap is present. If more than 2.5 wt % of the fatty acid is used in the instant compositions, the composition will become unstable at low temperatures as well as having an objectionable smell.

As example of the fatty acids which can be used as such or in the form of soap, mention can be made of distilled coconut oil fatty acids, "mixed vegetable" type fatty acids (e.g. high percent of saturated, mono-and/or polyunsaturated $C_{18}$ chains); oleic acid, stearic acid, palmitic acid, eiocosanoic acid, and the like, generally those fatty acids having from 8 to 22 carbon atoms being acceptable.

The carpet cleaning composition of this invention may, if desired, also contain other components either to provide additional effect or to make the product more attractive to the consumer. The following are mentioned by way of example: Colors or dyes in amounts up to 0.5% by weight; bactericides in amounts up to 1% by weight; preservatives or antioxidizing agents, such as formalin, 5-chloro-2-methyl-4-isothaliazolin-3-one, 2,6-di-tert.butyl-p-cresol, etc., in amounts up to 2% by weight; and pH adjusting agents, such as sulfuric acid or sodium hydroxide, as needed. Furthermore, if opaque compositions are desired, up to 4% by weight of an opacifier may be added.

The instant compositions of the instant invention explicitly exclude zwitterionic surfactant such as betaines because these zwitterionic surfactants are extremely high foaming which, if used in the instant composition, would cause the instant compositions to have to high a foam profile and that too much foam would leave residue on the carpet being cleaned.

Because the compositions as prepared are aqueous liquid formulations and since no particular mixing is required to form the compositions, the compositions are easily prepared simply by combining all the ingredients in a suitable vessel or container. The order of mixing the ingredients is not particularly important and generally the various ingredients can be added sequentially or all at once or in the form of aqueous solutions of each or all of the primary detergents and cosurfactants can be separately prepared and combined with each other and with the perfume. The magnesium salt, or other multivalent metal compound, when present, can be added as an aqueous solution thereof or can be added directly. It is not necessary to use elevated temperatures in the formation step and room temperature is sufficient.

The following examples illustrate liquid cleaning compositions of the described invention. Unless otherwise specified, all percentages are by weight. The exemplified compositions are illustrative only and do not limit the scope of the invention. Unless otherwise specified, the proportions in the examples and elsewhere in the specification are by weight.

EXAMPLE 1

The following compositions in wt. % were prepared:

| | A | B | C | D | E | F | Mr. Proper | St Marc Lemon |
|---|---|---|---|---|---|---|---|---|
| Sodium $C_{13}$–$C_{17}$ Paraffin sulfonate | 4.7 | 4.3 | 4 | 4.3 | 14.1 | 7.05 | 2.9 | — |
| EO/PO nonionic | — | — | — | — | — | — | — | 3.2 |
| Levenol F-200 | 2.3 | 2.2 | 2 | 2.2 | 6.3 | 3.45 | — | — |
| C13–C15 EO 14 nonionic | — | — | — | — | — | — | 3.3 | — |
| DEGMBE | 4 | 4 | 3.5 | 4 | 12 | 6 | 4.4 | 3 |
| Fatty acid | 0.75 | 0.5 | 0.4 | 0.75 | 2.25 | 1.125 | 0.65 | 0.3 |
| MgSO4 7H2O | 2.2 | 2 | 1.9 | 2.2 | 6.3 | 3.15 | — | — |
| Perfume (a) | 0.8 | 0.75 | 0.9 | 0.7 | 2.4 | 1.2 | present | present |
| Sodium Citrate | — | — | — | — | — | — | 3.2 | — |
| Water | Bal | Bal | Bal | Bal | Bal | Bal | Bal | Bal |
| pH | 7 | 7 | 7 | 7 | 7 | 7 | 9.5 | 7 |
| Degreasing test | | | | | | | | |
| Neat (b) | 30 | 35 | 35 | 35 | 30 | 30 | 70 | >100 |
| Dilute (b) | 45 | 60 | 60 | 60 | 45 | 45 | >90 | 90 |
| Residue | Equal to ref. | Equal to ref. | Equal to ref. | Equal to ref. | Equal to ref. | Equal to ref. | Worse | Equal to ref. |
| Foam in hard Water | Equal to ref. | Equal to ref. | Equal to ref. | Equal to ref. | Equal to ref. | Equal to ref. | Equal to ref. | Equal to ref. |
| LC50-Ecotoxicity on Daphniae (c) | 0.18 ml/l | — | — | — | — | — | 0.1 ml/l | 0.033 ml/l |

| | G | H | I | J | K | L |
|---|---|---|---|---|---|---|
| Linear alkyl benzene sulfonic acid C14–17 | 4.7 | 4.5 | 5 | 13.54 | 13.54 | 13.54 |
| NaOH to reach pH 7 | 0.6 | 0.57 | 0.64 | 0.6 | 0.6 | |
| Levenol F-200 | 2.3 | 2.5 | 2 | 6.62 | 6.62 | 6.62 |
| DEGMBE | 5.6 | 6 | 6.2 | — | — | 13 |
| Dipropylene glycol monobutyl ether | | | | 7.5 | | |
| Fatty acid | 0.75 | 0.75 | 0.75 | 2.16 | 2.16 | 2.16 |
| Dipropylene glycol monomethyl ether | | | | 5.5 | 8.7 | |
| PEG300 | | | | | 4.3 | |
| MgSO4 7H2O | 2.15 | 2.06 | 2.3 | — | — | |
| Perfume (a) | 0.8 | 0.8 | 0.8 | 2.3 | 2.3 | 2.3 |
| Water | Bal | Bal | Bal | Bal | Bal | Bal. |
| pH | 7 | 7 | 7 | 7 | 7 | 7 |

(a) contains 25% by weight of terpenes.
(b) the lower the number of strokes, the better the degreasing performance.
(c) the higher the results, the lower the ecotoxicity.

Furthermore, "dissolution power" of the o/w microemulsion of this example is compared to the "dissolution power" of an identical composition except that an equal amount (5 weight percent) of sodium cumene sulfonate hydrotrope is used in place of the diethylene glycol monobutyl ether cosurfactant in a test wherein equal concentrations of heptane are added to both compositions. The o/w microemulsion of this invention solubilizes 12 grams of the water immiscible substance as compared to 1.4 grams in the hydrotrope containing liquid composition.

In a further comparative test using blue colored cooking oil—a fatty triglyceride soil—, the composition of Example 1 is clear after the addition of 0.2 grams of cooking oil whereas the cooking oil floats on the top of the composition containing the sulfonate hydrotrope.

EXAMPLE 2

The example illustrates a typical formulation of a "concentrated" o/w microemulsion based on the present invention:

| | % by weight |
|---|---|
| Coco fatty acid | 4 |
| Sodium $C_{13}$–$C_{17}$ Paraffin Sulfonate | 20.75 |
| Levenol F-200 | 12 |
| Diethylene glycol monobutyl ether | 20 |
| Perfume (a) | 12.5 |
| Water | Bal to 100 |
| pH: 7.0 ± 0.2 | |

This concentrated formulation can be easily diluted, for example, five times with tap water, to yield a diluted o/w microemulsion composition. Thus, by using microemulsion technology it becomes possible to provide a product having high levels of active detergent ingredients and perfume, which has high consumer appeal in terms of clarity, odor and stability, and which is easily diluted at the usual usage concentration for similar all-purpose hard surface liquid cleaning compositions, while retaining its cosmetically attractive attributes.

Naturally, these formulations can be used, where desired, without further dilution and can also be used at full or diluted strength to clean soiled fabrics by hand or in an automatic laundry washing machine.

EXAMPLE 3

This example illustrates a diluted o/w microemulsion composition according to the invention having an acidic pH and which also provides improved cleaning performance on soap scum and lime scale removal as well as for cleaning greasy soil.

| | % by weight |
|---|---|
| Sodium $C_{13}$–$C_{17}$ paraffin sulfonate | 4.7 |
| Levenol F-200 | 2.3 |
| $MgSO_4$ $7H_2O$ | 2.2 |
| Mixture of succinic acid/glutaric acid/adipic acid (1:1:1) | 5 |
| Perfume (d) | 1.0 |
| Water, minors (dye) | balance to 100 |
| Phosphonic acid | 0.2 |
| Amino tris-(methylene-phosphonic acid) | 0.03 |
| pH = 3 ± 0.2 | |

(d) contains 40% by weight of terpene

EXAMPLE 4

Formula A of Example I was tested for the removal of a combination of grease and particulate soil as well as for a grease release effect and compared to commercial Ajax™NME I. Grease+particulate soil removal;

Test Method

A) Soil composition:

70 g of mineral oil 35 g of particulate soil (vacuum cleaner dust+1% of carbon black)

35 g $C_2Cl_4$

B) Soil preparation:

Weigh cleaned/dried glass tiles

Soil the tiles with the grease+particulate soil

Bake the tiles 1 hour at 80° C.

Weigh the soiled tiles which aged 2 hours at RT.

C) Soil removal:

The soiled tiles are soaked for 15 minutes at RT in the test products, then they are delicately rinsed with tap water.

After drying 45 minutes at 50° C., the tiles are weighed again.

Results

| | Grease + particulate soil % of removal mean of 6 tiles |
|---|---|
| Commercial Ajax ™ NME | 60 |
| Formula A of Example I | 95 |

Formula A exhibits improved grease+particulate soil removal over the Commercial Ajax™ NME II. Grease release effect Test Method A) Soil composition:

20% hardened tallow

80% beef tallow fat blue dye

B) Soil preparation:

The fat mixture is heated and sprayed with an automatic spraying device on cleaned and dried ceramic tiles.

C) Soil removal:

Product used neat: 2.5 g on sponge

Product used dilute: 1.2% sol in tap water—10 ml of the solution on the sponge. The cleaning procedure is done with the gardner device for both product concentrations.

Results

A) On treated ceramic tiles (treated with the product before spraying the soil)

| | Neat | Dilute |
|---|---|---|
| | Number of Strokes | |
| First grease layer deposition | mean of 4 tiles | mean of 6 tiles |
| Commercial Current Ajax ™ NME | 27 | 19 |
| | 19 | 5* |
| Second grease layer deposition on the same tile | mean of 4 tiles | mean of 6 tiles |
| Commercial Ajax ™ NME | 25 | 48 |
| | 25 | 18* |

B) On untreated ceramic tiles

In addition to the previous test, the 3 following procedures were used to verify that Formula A remains on the surface after rinsing or wiping. After the first cleaning procedure and before the second spraying:

1) the tiles were allowed to dry in open air
2) the surface was wiped with paper towel
3) the surface was rinsed with wet sponge
1) dry in open air

| | Neat | Dilute |
|---|---|---|
| | Number of Strokes | |
| First grease layer deposition | mean of 4 tiles | mean of 6 tiles |
| Commercial Ajax ™ NME | 29 | 30 |
| Formula A | 27 | 32 |
| Second grease layer deposition on the same tile | mean of 4 tiles | mean of 6 tiles |
| Commercial Ajax ™ NME | 33 | 21 |
| Formula A | 30 | 6* |

2) wipe dry the surface

|  | Neat | Dilute |
|---|---|---|
|  | Number of Strokes | |
| First grease layer deposition | mean of 4 tiles | mean of 6 tiles |
| Commercial Ajax ™ NME | 29 | 30 |
| Formula A | 27 | 32 |
| Second grease layer disposition on the same tile | mean of 4 tiles | mean of 6 tiles |
| Commercial Ajax ™ NME | 35 | 46 |
| Formula A | 30 | 48.5 |

3) wet wiping the surface

|  | Neat | Dilute |
|---|---|---|
|  | Number of Strokes | |
| First grease layer deposition | mean of 4 tiles | mean of 6 tiles |
| Commercial Ajax ™ NME | 29 | 30 |
| Formula A | 27 | 32 |
| Second grease layer deposition on the same tile | mean of 4 tiles | mean of 6 tiles |
| Commercial Ajax ™ NME | 34 | 58 |
| Formula A | 27 | 41** |

*highly significant difference
**after 5 strokes, 65% of the grease is already removed These results clearly demonstrate the important grease release effect obtained with Formula A especially when the product is used dilute.

EXAMPLE 5

The following liquid crystal compositions were prepared by simple mixing procedure

|  | A | B | C |
|---|---|---|---|
| Sodium $C_{13}$–$C_{17}$ Paraffin sulfonate | 4.3 | 4.3 | 4.3 |
| Levenol F-200 | 2.2 | 2.2 | 2.2 |
| Propylene glycol monobutyl ether | 3.5 | — | — |
| Dipropylene glycol monbutyl ether | — | 3.5 | — |
| Tripropylene glycol monbutyl ether | — | — | 3.5 |
| Fatty acid | 0.5 | 0.5 | 0.5 |
| MgSO4 7H2O | 1.6 | 1.6 | 1.6 |
| Perfume (a) | 1 | 1.5 | 1.5 |
| Water | Bal | Bal | Bal |
| pH | 7 | 7 | 7 |

EXAMPLE 6

The following optically clear microemulsion compositions were made by forming first a solution by mixing at 25° C. water, magnesium lauryl ether sulfate, Levenol V-510/2 and 1-Pentanol. To this solution with mixing at 25° C. was added the dodecane to form the optically clear microemulsion. The formula are expressed in weight percent.

|  | A | B | C | D | E | F | G | H | I |
|---|---|---|---|---|---|---|---|---|---|
| Magnesium Lauryl sulfate | 7 | 2.04 | 3.04 | 4.99 | 3.01 | 6.38 | 5.01 | 4.02 | 2.99 |
| Levenol V-501/2 | 3.2 | 8.15 | 7.1 | 5.1 | 7.06 | 3.9 | 5.06 | 6.24 | 7.2 |
| 1-Pentanol | 1.19 | 1.03 | 4.1 | 4.05 | 5.05 | 5.67 | 1.07 | 1.05 | 1.13 |
| Dodecane | 1.29 | 0.73 | 17.36 | 11.26 | 20.07 | 15.2 | 2.86 | 3.05 | 2.9 |
| water | Bal | Bal | Bal | Bal | Bal | Bal | Bal | Bal | Bal |

EXAMPLE 7

The following carpet cleaning formula was made by simple mixing at 25° C.

|  | Wt. % |
|---|---|
| Deionized water | 80.93 |
| $C_{14-17}$ paraffin sulfonate sodium | 3.92 |
| Esterified polyethoxyether | 1.15 |
| Magnesium sulfate heptahydrate | 1.10 |
| Diethylene glycol monobutyl ether | 2.00 |
| Stripped coconut oil fatty acids No. 2 | 0.37 |
| 38% Na2O caustic soda | 0.030 |
| N-silicate (1:3.26) | 0.20 |
| Perfume Firmenich (a) | 0.21 |
| Hydrocarbon propellant mixture | 10.00 |
| Benzyl benzoate | 0.09 |

In summary, the described invention broadly relates to an improvement in microemulsion compositions containing an anionic surfactant, an esterified polyethoxyether nonionic surfactant, an acaricidal agent, a fatty acid, one of the specified cosurfactants, a hydrocarbon ingredient and water.

What is claimed is:

1. A carpet cleaning composition comprising:
   (a) 0.1 wt. % to 20 wt. % of a mixture of

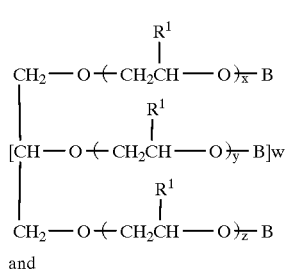

(I)

and

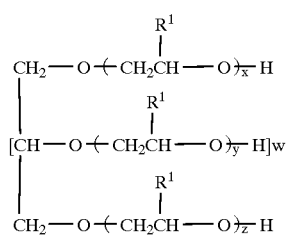

(II)

wherein w equals one to four, B is selected from the group consisting of hydrogen and a group represented by:

wherein R is selected from the group consisting of alkyl group having 6 to 22 carbon atoms, and alkenyl groups having 6 to 22 carbon atoms, wherein at least one of the B groups is represented by said

R' is selected from the group consisting of hydrogen and methyl groups; x, y and z have a value between 0 and 60, provided that (x+y+z) equals 2 to 100, wherein in Formula (I) the weight ratio of monoester/diester/triester is 45 to 90/5 to 40/1 to 20, wherein the weight ratio of Formula (I) to Formula (II) is a value between 3 and 0.02;

(b) 0.1 wt. % to 20 wt. % of an anionic surfactant, wherein the surfactant is a sulfate or sulfonate surfactant;
 (c) 0.1 wt. % to 50 wt. % of at least one glycol ether cosurfactant;
 (d) 0.1 wt. % to 10 wt. % of a water insoluble hydrocarbon, essential oil or a perfume, wherein said composition further comprises;
 (e) 0.05 wt. % to 5 wt. % of an acaricidal agent; and
 (f) the balance being water, wherein the composition does not contain a solid component having a mean particle size of 2 to 100 microns which would leave a pulverulent residue on the surface being treated or quartz, sand, siliceous earth, metal carbonate, $SiO_2$, amorphous silica, silicates, polyacrylates, xanthan gum or aliphatic alcohols, alkyl aryl alcohols, alkanol amines, amines, polyhexamethylene biquamide hydrochloride, didecyl dimethyl ammonium chloride, benzyalkonium chloride, isopropyl alcohol and N-lower alkyl neoalkanolamides.

2. The carpet cleaning composition of claim 1 which further contains a salt of a multivalent metal cation in an amount sufficient to provide from 0.5 to 1.5 equivalents of said cation per equivalent of said anionic surfactant.

3. The carpet cleaning composition of claim 2 wherein the multivalent metal cation is magnesium or aluminum.

4. The carpet cleaning composition of claim 2, wherein said composition contains 0.9 to 1.4 equivalents of said cation per equivalent of anionic surfactant.

5. The carpet cleaning composition of claim 2 wherein said salt is magnesium oxide, magnesium chloride or magnesium sulfate.

6. The carpet cleaning composition of claim 1 wherein the cosurfactant is a water soluble glycol ether.

7. The carpet cleaning composition of claim 6 wherein the glycol ether is selected from the group consisting of ethylene glycol monobutyl ether, diethylene glycol monobutyl ether, triethylene glycol monobutyl ether, propylene glycol tert-.butyl ether, mono, di, or tri propylene glycol monobutyl ether, and mono di or tri propylene glycol monomethyl ether and mixtures thereof.

8. The carpet cleaning composition of claim 6 wherein the glycol ether is ethylene glycol monobutyl ether or diethylene glycol monobutyl ether.

9. The carpet cleaning composition of claim 1 wherein the anionic surfactant is a $C_9$–$C_{15}$ alkyl benzene sulfonate or a $C_{13}$–$C_{17}$ paraffin sulfonate.

10. The carpet cleaning composition of claim 1 further including a fatty acid which has 8 to 22 carbon atoms.

11. The carpet cleaning composition according to claim 1 further including 0 to 20 wt. % of a hydrocarbon propellant.

* * * * *